US009555950B2

(12) United States Patent
Le Maner et al.

(10) Patent No.: US 9,555,950 B2
(45) Date of Patent: Jan. 31, 2017

(54) FLUID PRODUCT DISPENSING DEVICE

(71) Applicant: APTAR FRANCE SAS, Le Neubourg (FR)

(72) Inventors: Francois Le Maner, La Haye-Malherbe (FR); Jurgen Greiner-Perth, Gottmadingen (DE); Silvio Carrico, Singen (DE); Matthias Wochele, Friolzheim (DE)

(73) Assignee: APTAR FRANCE SAS, Le Neubourg (FR)

( * ) Notice: Subject to any disclaimer, the term of this patent is extended or adjusted under 35 U.S.C. 154(b) by 0 days.

(21) Appl. No.: 14/765,907

(22) PCT Filed: Mar. 18, 2014

(86) PCT No.: PCT/FR2014/050618
§ 371 (c)(1),
(2) Date: Aug. 5, 2015

(87) PCT Pub. No.: WO2014/147329
PCT Pub. Date: Sep. 25, 2014

(65) Prior Publication Data
US 2016/0068326 A1    Mar. 10, 2016

(30) Foreign Application Priority Data

Mar. 19, 2013  (FR) .................................... 13 52460

(51) Int. Cl.
*B65D 83/00*  (2006.01)
*A61M 15/00*  (2006.01)
(Continued)

(52) U.S. Cl.
CPC ........ *B65D 83/0005* (2013.01); *A61M 11/007* (2014.02); *A61M 15/0065* (2013.01);
(Continued)

(58) Field of Classification Search
CPC ............ B65D 83/0005; B65D 2203/12; A61M 11/007; A61M 15/0065; A61M 15/08; A61M 15/004; A61M 15/0036; A61M 2205/584; B05B 11/025; B05B 11/308; B05B 11/02
(Continued)

(56) References Cited

U.S. PATENT DOCUMENTS 4,817,822 A * 4/1989 Rand .................... A61M 15/009
128/200.14
5,542,411 A * 8/1996 Rex .................... A61M 15/0028
128/203.12
(Continued)

FOREIGN PATENT DOCUMENTS

EP  0 254 391 A1  1/1988
EP  0 580 897 A1  2/1994
(Continued)

OTHER PUBLICATIONS

International Search Report for PCT/FR2014/050618 dated Jul. 7, 2014.
(Continued)

*Primary Examiner* — Donnell Long
(74) *Attorney, Agent, or Firm* — Sughrue Mion, PLLC

(57) ABSTRACT

A fluid dispenser device comprising: a reservoir (10) containing at least two doses of fluid; a dispenser member (20), such as a piston, that is mounted to slide in said reservoir (10) so as to dispense the fluid; a dispenser head (30) that is provided with a dispenser orifice (31), said head being movable relative to said reservoir (10) so as to move said actuator member (20) in said reservoir (10) and thus dispense the fluid through said dispenser orifice (31); said dispenser head (30) including at least two viewing windows (35, 36), said device including an indicator (40) that is movable together with said reservoir (10), said indicator (Continued)

(40) co-operating with a respective viewing window (35, 36) after each actuation of the device.

7 Claims, 2 Drawing Sheets

(51) Int. Cl.
*A61M 15/08* (2006.01)
*B05B 11/02* (2006.01)
*B05B 11/00* (2006.01)
*A61M 11/00* (2006.01)

(52) U.S. Cl.
CPC ............ *A61M 15/08* (2013.01); *B05B 11/02* (2013.01); *B05B 11/025* (2013.01); *B05B 11/308* (2013.01); *A61M 15/004* (2014.02); *A61M 15/0036* (2014.02); *A61M 2205/584* (2013.01); *B65D 2203/12* (2013.01)

(58) Field of Classification Search
USPC .................... 222/321.6, 160, 23, 41, 47
See application file for complete search history.

(56) References Cited

U.S. PATENT DOCUMENTS

| | | | |
|---|---|---|---|
| 6,142,339 A * | 11/2000 | Blacker | A61M 15/009 128/200.23 |
| 6,164,494 A * | 12/2000 | Marelli | G06M 1/241 222/36 |
| 6,708,846 B1 | 3/2004 | Fuchs et al. | |
| 2002/0010428 A1* | 1/2002 | Vedrine | A61M 11/06 604/187 |
| 2005/0015051 A1 | 1/2005 | Stadelhofer | |
| 2005/0211241 A1* | 9/2005 | Anderson | A61M 15/08 128/200.22 |
| 2012/0031401 A1* | 2/2012 | Berger | A61M 15/08 128/203.12 |

FOREIGN PATENT DOCUMENTS

| | | | | |
|---|---|---|---|---|
| FR | 2 652 981 A1 | 7/1989 | | |
| FR | 2625981 A1 * | 7/1989 | .......... | A61M 5/2429 |

OTHER PUBLICATIONS

International Preliminary Report on Patentability dated Sep. 24, 2015, issued by the International Bureau in corresponding International Application No. PCT/FR2014/050618.

\* cited by examiner

FLUID PRODUCT DISPENSING DEVICE

CROSS REFERENCE TO RELATED APPLICATIONS

This application is a National Stage of International Application No. PCT/FR2014/050618 filed Mar. 18, 2014, claiming priority based on French Patent Application No. 1352460 filed Mar. 19, 2013, the contents of all of which are incorporated herein by reference in their entirety.

The present invention relates to a fluid dispenser device, and more particularly to a device of the dual-dose type.

The term "dispenser device of the dual-dose type" means a device containing two doses of fluid to be dispensed during two successive actuations of the dispenser device.

Devices of the dual-dose type are well known in the state of the art. Such devices generally comprise a reservoir containing the two doses of fluid to be dispensed, and a dispenser member that is generally a piston, that is mounted to slide in said reservoir, and that is moved so as to dispense the fluid contained in said reservoir. In a dual-dose device, the piston is moved in two successive actuation strokes, such that a first dose is dispensed during a first actuation, and a second dose is dispensed during a second actuation. With this type of dual-dose device, it is sometimes difficult for the user to know whether the device has dispensed one or two doses. Unfortunately, depending on the type of fluid that is dispensed by the device, in particular when it is a medication, it may be important to avoid any risk of under-dosing and/or of over-dosing. Thus, by way of example, if the device of the dual-dose type is for dispensing a respective dose into each nostril, it is not generally desirable for both doses to be dispensed into the same nostril. Unfortunately, a user who has used the device to dispense a first dose into a first nostril, and who has then put it down or who has been distracted, risks dispensing the second dose into the same nostril as the first dose if it is not clear that the device has already been used a first time. This is not generally desirable. Thus, if the fluid is expelled twice into the same nostril, the excess active ingredient is not properly absorbed by the tissues, or immediately starts to run out of the nostril, with a clear loss of effectiveness. Furthermore, no dose is then available for the second nostril. Documents EP 0 254 391, FR 2 625 981, U.S. Pat. No. 6,708,846, EP 0 580 897, and US 2005/015051 describe prior-art devices.

An object of the present invention is to provide a fluid dispenser device that does not have the above-mentioned drawbacks.

Another object of the present invention is to provide a fluid dispenser device that indicates to the user, in reliable manner, the number of doses to be dispensed.

Another object of the present invention is to provide such a fluid dispenser device that is simple and inexpensive to manufacture and to assemble.

The present invention thus provides a fluid dispenser device comprising: a reservoir containing at least two doses of fluid; a dispenser member, such as a piston, that is mounted to slide in said reservoir so as to dispense the fluid; a dispenser head that is provided with a dispenser orifice, said head being movable relative to said reservoir so as to move said actuator member in said reservoir and thus dispense the fluid through said dispenser orifice; said dispenser head including at least two viewing windows, said device including an indicator that is movable together with said reservoir, said indicator co-operating with a respective viewing window after each actuation of the device.

Advantageously, the reservoir contains two doses of fluid that are dispensed during two successive actuations of the device, said dispenser head including two viewing windows.

Advantageously, said indicator co-operates with a first viewing window after the first dose of fluid has been dispensed, and with a second viewing window after the second dose of fluid has been dispensed.

In a first advantageous variant, said indicator comprises at least one colored indication zone, said indication zone appearing in said first viewing window after the first dose of fluid has been dispensed, and in the second viewing window after the second dose of fluid has been dispensed.

In a second advantageous variant, said indicator is adapted to mask colored indication zones that are provided in said dispenser head, said indicator masking a colored indication zone in said first viewing window after the first dose of fluid has been dispensed, and masking a colored indication zone in said second viewing window after the second dose of fluid has been dispensed.

Advantageously, after the second dose of fluid has been dispensed, said indicator co-operates with both viewing windows.

Advantageously, said indicator is formed on a body that is fastened to said reservoir.

Advantageously, said indicator is adapted to indicate, through at least one viewing window, that an incomplete dose has been dispensed.

These advantages and characteristics and others of the present invention appear more clearly from the following detailed description, given by way of non-limiting examples, and with reference to the accompanying drawings, and in which:

FIGS. 1, 2, and 3 are diagrammatic section views of a fluid dispenser device in a first advantageous variant embodiment of the present invention, respectively before dispensing the first dose, after dispensing the first dose, and after dispensing the second dose;

Figure 6:
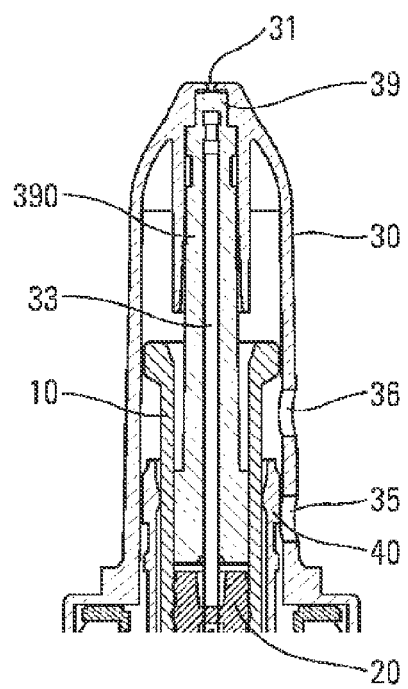
Figure 7:
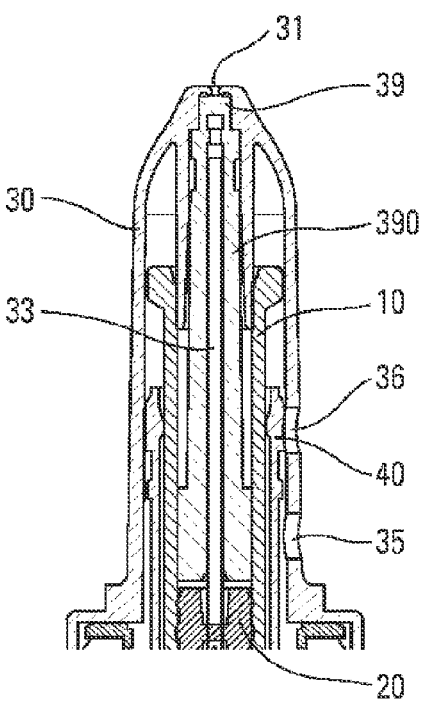
Figure 8:
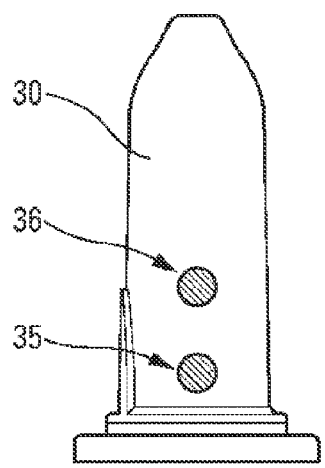
Figure 9:
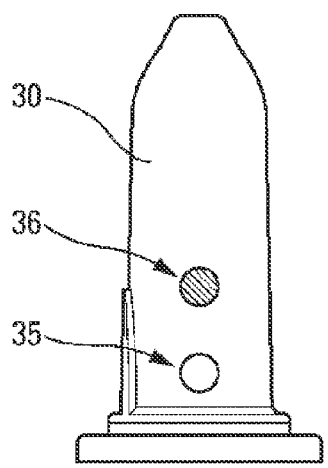
Figure 10:
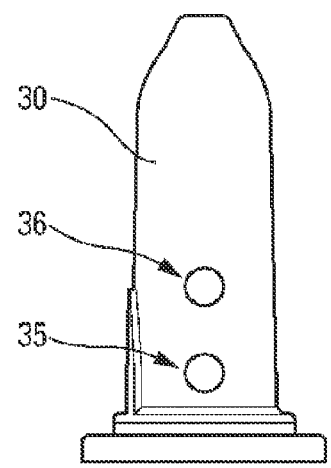

FIGS. 6 and 7 are diagrammatic and fragmentary section views of a second variant embodiment of the invention, respectively after dispensing the first dose, and after dispensing the second dose; and FIGS. 8 to 10 are diagrammatic side views of the dispenser head in FIGS. 6 and 7, showing the visual indication that can be seen by the user, respectively before dispensing the first dose, after dispensing the first dose, and after dispensing the second dose.

The present invention is described below with reference to a dual-dose embodiment, i.e. a device containing two doses of fluid to be dispensed during two successive actuations of the device. However, the present invention could naturally apply to devices that contain any number of doses, e.g. three or four doses. In addition, the dual-dose type device shown in the drawings is only one possible embodiment to which the present invention applies, and naturally the present invention applies more generally to any type of device containing at least two doses.

Figures 1, 2, 3:
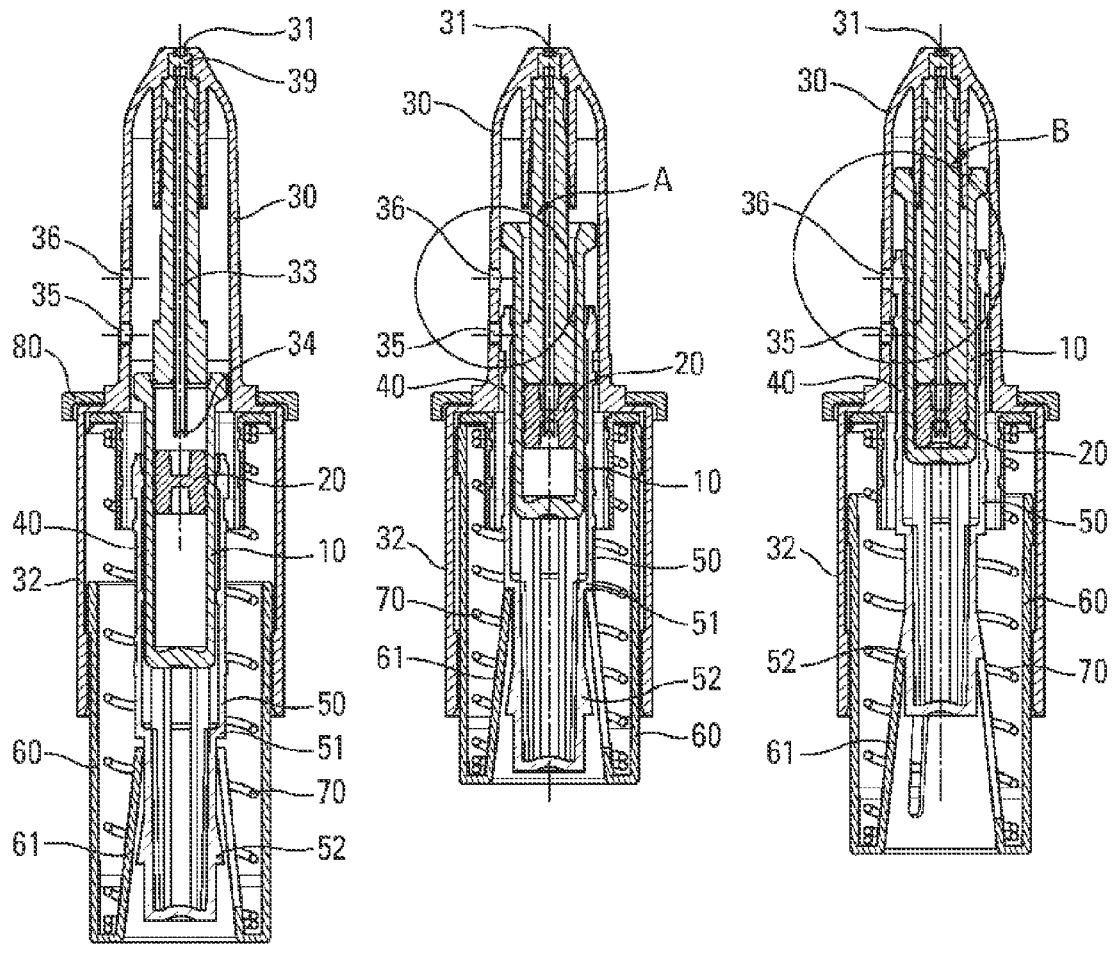
Figures 4, 5:
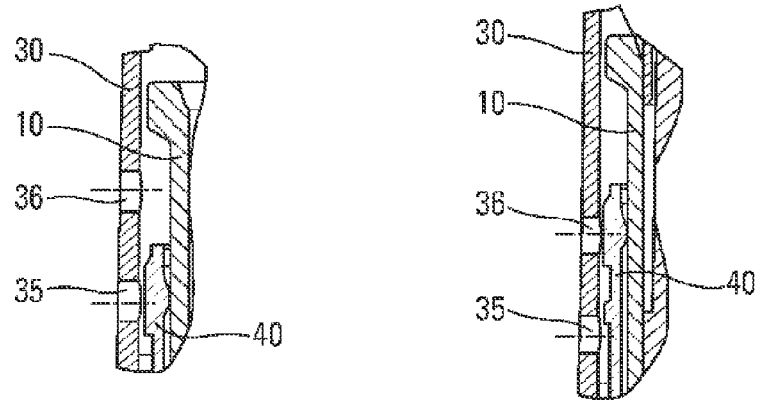
FIG. 4 is a larger-scale view of a detail A of FIG. 2.
FIG. 5 is a larger-scale view of a detail B of FIG. 3.

With reference to FIGS. 1 to 3, the dual-dose dispenser device includes a reservoir 10 containing two doses of fluid. A dispenser member, such as a piston 20, is mounted to slide in said reservoir 10. In the pre-actuation position of the device, shown in FIG. 1, said piston 20 acts as a stopper, isolating the contents of the reservoir 10.

A dispenser head 30 is assembled on said reservoir 10, being axially movable relative to said reservoir. In particular, an axial movement of the dispenser head 30 relative to the reservoir 10 causes the piston 20 to move in the reservoir 10, and thus causes the fluid contained in said reservoir to be dispensed. The dispenser head 30 includes a dispenser channel 33 that extends from a perforator tip 34 to the dispenser orifice 31 of the dispenser head 30. Upstream of the dispenser orifice 31, there may be provided a spray profile 39 for dispensing the fluid in the form of spray, which profile may be of any known type and is not shown in greater detail in the drawings.

More precisely, in the embodiment shown, the reservoir 10 is fastened in a body 50 that is thus secured to said reservoir 10 and that moves together with said reservoir.

The dispenser head 30 includes a bottom side skirt 32 that is adapted to co-operate with an actuator member 60. A finger-rest element 80 may be assembled around said dispenser head 30, or, in a variant, may be formed integrally therewith.

Said actuator member 60 is axially movable inside said side skirt 32 of the dispenser head 30 so as to perform successive actuations of the device. As can be seen in particular in FIG. 1, the actuator member 60 includes at least one sloping tab 61 that is adapted to co-operate with projections 51, 52 of the body 50 so as to perform successive actuations.

A return spring 70 is mounted between the actuator member 60 and the dispenser head 30 so as to return said actuator member 60 into its start position after each actuation.

Operation of the device shown in FIGS. 1 to 3 is as follows. In the rest position in FIG. 1, the stopper piston 20 isolates the contents of the reservoir 10 from the atmosphere. When the user presses simultaneously on the finger rest 80 and on the actuator member 60, said actuator member 60 moves inside the side skirt 32 of the dispenser head 30. This pushes the body 50 axially upwards from the position shown in FIG. 1, by means of the tabs 61 that push on the shoulder 51 of said body. This compresses the spring 70 and moves the reservoir 10 relative to the dispenser head 30. When the reservoir 10 starts to move relative to the dispenser head 30, the perforator end 34 of the dispenser channel 33 comes to perforate the stopper piston 20 so as to put the inside of the reservoir 10 into communication with said expulsion channel 33. Continued actuation causes the piston 20 to move inside the reservoir, thereby causing the first dose to be dispensed. The fluid is thus pushed by said piston 20 through the perforator end 34 and into the dispenser channel 33, then via the spray profile 39 and out of the device through the dispenser orifice 31.

After the first dose has been dispensed, the device is in the position shown in FIG. 2, and when the user releases the actuator member 60, the spring 70 returns said actuator member towards its start position. While the actuator member 60 is returning, the reservoir and the body 50 do not move back, since the two components remain held in said dispenser head 30. Optionally, the dispenser head 30 may include non-return means, so as to prevent said body 50 and/or said reservoir 10 from moving back. When the actuator member 60 returns towards its rest position under the effect of the return spring 70, the tabs 61 come to snap-fasten below the second projection 52 of the body 50, which enables the user to actuate the device a second time, so as to dispense the second dose of fluid.

FIG. 3 shows the position after the second dose has been dispensed.

In the invention, the dispenser device includes an indicator 40 for indicating to the user whether the first dose has been dispensed and whether the second dose has been dispensed. In this way, the user knows exactly what the situation is, and whether or not the first dose has been dispensed. The indicator 40 is adapted to co-operate with viewing windows 35, 36 that are formed in said dispenser head 30. Advantageously, the viewing windows 35, 36 are formed in a side wall of the head, clearly visible to the user when the device is held in the hand. Naturally, if the number of doses of fluid contained in the reservoir is different from two, then the number of viewing windows is also different from two. In particular, the viewing windows may be made in the form of holes that pass through the wall of the dispenser head 30, as shown in figures.

Advantageously, said indicator 40 is formed on said body 50 that is fastened to the reservoir 10. However, in a variant it is possible to imagine an indicator 40 that is formed directly on the reservoir 10.

In a first advantageous variant, the indicator 40 comprises at least one colored zone that comes to be displayed behind the viewing windows 35, 36 after successive actuations of the device.

Thus, as can be seen in FIG. 1, before actuation, no portion of the indicator 40 is visible behind the viewing windows 35, 36. After the first dose has been dispensed, as shown in FIG. 2, the indicator 40 has moved relative to the dispenser head 30, so as to come to be positioned behind the first viewing window 35. Advantageously, the colored zone, typically red, of the indicator 40 thus indicates to the user, by a red display in the first viewing window 35, that the first dose has been dispensed, whereas the display in the second viewing window 36 remains unchanged. After the second dose has been dispensed, said indicator 40 follows its axial movement relative to the dispenser head 30, so as to come to be positioned behind the second viewing window 36. In this embodiment, after the second dose has been dispensed, the indicator advantageously co-operates with both viewing windows 35, 36, i.e. the user sees the colored zone in both windows 35, 36.

Thus, in summary, before the device is actuated for the first time, both viewing windows 35, 36 have a display that appears blank, e.g. white. After the first dose has been dispensed, the first viewing window 35 becomes red, whereas the second viewing window 36 remains blank. After the second dose has been dispensed, both viewing windows 35, 36 are red. The user thus has no difficulty in seeing very quickly whether or not the first and/or the second dose has/have been dispensed, and thus does not risk overdosing and/or under-dosing the fluid, e.g. by dispensing the fluid twice into the same nostril.

In a second advantageous variant, the indicator 40 does not include a colored zone, but, on the contrary, is made in the same color as the dispenser head 30. In this second variant, the indicator 40 is adapted to mask colored indication zones that are visible through the viewing windows 35, 36 before actuation. Thus, the colored indication zones may be provided on a part that is secured to the dispenser head, in particular on the rod element 390 that is in contact with the piston 20. In particular, the rod element 390 may be made entirely out of colored material. The reservoir 10 is thus advantageously transparent so that said colored indication zones can be seen in the viewing windows 35, 36 before actuation. Before the first actuation, both viewing windows 35 and 36 display a colored dot, as can be seen in FIG. 8. After the first actuation, the indicator 40 masks the first viewing window 35, such that only the second viewing window 36 displays a colored dot, as can be seen in FIG. 9. After the second actuation, the indicator 40 masks both viewing windows 35 and 36, such that neither viewing window displays a colored dot, as shown in FIG. 10.

Thus, in summary, before the device is actuated for the first time, both viewing windows 35, 36 have a colored display, e.g. red or blue. After the first dose has been dispensed, the colored zone behind the first viewing window 35 is masked, whereas the display of the second viewing window 36 remains unchanged. After the second dose has been dispensed, the colored zones behind both viewing windows 35, 36 are masked by the indicator 40. The user thus has no difficulty in seeing very quickly whether or not the first and/or the second dose has/have been dispensed, and thus does not risk over-dosing and/or under-dosing the fluid, e.g. by dispensing the fluid twice into the same nostril.

Advantageously, the indicator 40 also makes it possible to indicate incomplete dispensing, in particular by sizing the viewing windows 35, 36 appropriately. Thus, only completely dispensed doses enable the indicator to fill the surface area of said windows completely. The user can then detect incomplete dispensing by means of the viewing window under consideration giving an indication that is only partial.

Naturally, the present invention is described above with reference to two non-limiting variant embodiments, and any useful modification can be applied to the present invention without going beyond its ambit, as defined by the accompanying claims.

The invention claimed is:

1. A fluid dispenser device comprising: a reservoir containing two doses of fluid; a dispenser member, formed by a piston, that is mounted to slide in said reservoir so as to dispense the fluid, said piston being movable relative to said reservoir between a rest position, before the first dose has been dispensed, and a final position, after the second dose has been dispensed; and a dispenser head that is provided with a dispenser orifice, said head being movable relative to said reservoir so as to move said actuator member in said reservoir and thus dispense the fluid through said dispenser orifice; the fluid dispenser device being characterized in that said dispenser head includes two viewing windows, said device including an indicator that is movable together with said reservoir, said indicator co-operating with a respective viewing window after each actuation of the device.

2. A device according to claim 1, wherein said indicator co-operates with a first viewing window after the first dose of fluid has been dispensed, and with a second viewing window after the second dose of fluid has been dispensed.

3. A device according to claim 2, wherein said indicator comprises at least one colored indication zone, said indication zone appearing in said first viewing window after the first dose of fluid has been dispensed, and in the second viewing window after the second dose of fluid has been dispensed.

4. A device according to claim 2, wherein said indicator is adapted to mask colored indication zones that are provided in said dispenser head, said indicator masking a colored indication zone in said first viewing window after the first dose of fluid has been dispensed, and masking a colored indication zone in said second viewing window after the second dose of fluid has been dispensed.

5. A device according to claim 2, wherein, after the second dose of fluid has been dispensed, said indicator co-operates with both viewing windows.

6. A device according to claim 1, wherein said indicator is formed on a body that is fastened to said reservoir.

7. A device according to claim 1, wherein said indicator is adapted to indicate, through at least one viewing window, that an incomplete dose has been dispensed.

* * * * *